US006455546B2

(12) United States Patent
Cross

(10) Patent No.: US 6,455,546 B2
(45) Date of Patent: *Sep. 24, 2002

(54) METHOD FOR PROMOTING OVULATION, PARTURITION, AND LACTATION IN MAMMALS

(75) Inventor: Dee L. Cross, Central, SC (US)

(73) Assignee: Clemson University, Clemson, SC (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/783,114

(22) Filed: Feb. 14, 2001

Related U.S. Application Data

(62) Division of application No. 08/768,981, filed on Dec. 18, 1996, now Pat. No. 6,224,895.

(51) Int. Cl.$^7$ ...................... A01N 43/40; A61K 31/445; A23K 1/165
(52) U.S. Cl. ...................... 514/322; 514/322; 514/277; 514/437; 514/450; 514/276; 424/442
(58) Field of Search .................. 424/442; 514/276, 514/322, 450, 277, 437

(56) References Cited

U.S. PATENT DOCUMENTS

| | | | |
|---|---|---|---|
| 4,005,211 A | | 1/1977 | Marsboom |
| 4,066,772 A | | 1/1978 | Vandenberk et al. |
| 4,755,519 A | | 7/1988 | Dougherty et al. |
| 4,847,243 A | | 7/1989 | Wallace |
| 4,880,632 A | | 11/1989 | Lipham et al. |
| 5,372,818 A | * | 12/1994 | Cross et al. ............ 424/442 |
| 6,224,895 B1 | * | 5/2001 | Cross .................. 424/442 |

FOREIGN PATENT DOCUMENTS

| | | |
|---|---|---|
| EP | 0297191 A1 | 1/1989 |
| EP | 0368000 A1 | 5/1990 |
| EP | 848954 A1 * | 6/1998 |

OTHER PUBLICATIONS

Redmond et al., Efficacy of Domperidone and Sulpiride As Treatments for Fescue Toxicosis in Horses. Am. J. Vet. Res. 55, 722–729 (May 1994).*

The Effect of Prepartum and Postpartum Oral Domperidone Therapy on Mares Consuming Endophyte–Infested Fescue, Kouba et al., 87th Annual Meeting, Journal of Animal Science, vol. 73, Supplement 1, Jul. 25–28, Orlando, Florida.

Jenner, et al.; "Steroselective actions of substituted benzamide drugs on cerebral dopamine mechanisms"; pp. 39–45; May 17, 1979.

Rossi, et al.; "Pharmacotoxicological Aspects of Levosulpiride"; pp. 81–94; *Pharmacological Research*, vol. 31, No. 2; 1995.

Elliott, et al.; "Substituted Benzamides as Cerebral Dopamine Antagonists in Rodents"; pp. 333–342; *Neuropharmacology*, 1977.

de Munain, et al.; "Tardive Akathisia Due to Sulpiride"; pp. 481–783; *Clinical Neruropharmacology*; vol. 17, No. 5; 1994.

Martensz, et al.; "Drug–Induced Hyperprolactinaemia and Discharges of Luteinizing Hormone Evoked By Oestrogen in Ovariectomized Rhesus Monkeys"; pp. 111–122; *Journal of Endocrinology*; 1982.

Massara, et al.; "Increased thyrotrophin and prolactin secretion induced by domperidone in hypothyroid subjects"; pp. 48–53.

Ferrari, et al.; "Behavioural Evidence for Central D–2 Dopamine Receptor Agonistic Effect by Some 2–(Fluorohydroxphenyl)Ethylamines"; pp. 131–134; *Pharmacology Biochemistry & Behavior*, vol. 38; 1991.

European Search Report; Apr. 9, 1998.

European Journal of Obstretrics, Gynocology and . . . ; pp. 283–287; vol. 19, No. 5, May, 1985.

"Dopaminergic regulation Of Gonadotrophin Secretion In Seasonally Anoestrous Mares", B. Besonet, et al., *Journal Of Reproduction And Fertility* (1996) 108, pp. 55–61.

Minireview, "The Pharmacology Of Sulpiride—A Dopamine Receptor Antagonist", S.E. O'Connor, et al., *General Pharmacology*, 1982, 13/3, pp. 185–193.

"Systemic Sulpiride Increases Dopamine Metabolites In The Lateral Hypothalamus", T. Baptista, et al.

Entry #3476 The Merck Index, Twelfth Ed., 1996, p. 578.

"Barrier membranes at the outer surface of the brain of an elasmobranch, Raja erinacea", Magnus Bundgaard, et al., *Cell and Tissue Research*, 1991, pp. 113–120.

"Morphology of Glial Blood–Brain Barrriers", Nancy J. Lane, *Annals New York Academy of Sciences*, pp. 348–362.

* cited by examiner

*Primary Examiner*—Karen Cochrane Carlson
*Assistant Examiner*—Chih-Min Kam
(74) *Attorney, Agent, or Firm*—Dority & Manning

(57) ABSTRACT

The present invention generally relates to various methods for promoting ovulation, parturition and lactation in female mammals. These benefits are obtained by administering to the mammals a composition containing a $D_2$ receptor antagonist that does not substantially cross the blood brain barrier. In one embodiment, the $D_2$ receptor antagonist is domperidone. The domperidone can be administered to the mammal either orally or subcutaneously and can be used to treat, for instance, anestrous mammals, mammals that have problems bearing offspring and mammals suffering from agalactia. Unexpectedly, it has also been discovered that the $D_2$ receptor antagonist may also stimulate feed intake, causing the mammal to eat more and gain weight faster.

7 Claims, No Drawings

METHOD FOR PROMOTING OVULATION, PARTURITION, AND LACTATION IN MAMMALS

RELATED APPLICATION

This application is a divisional of prior application Ser. No. 08/768,981, filed on Dec. 18, 1996, which issued as U.S. Pat. No. 6,224,895.

FIELD OF THE INVENTION

The present invention generally relates to a method for promoting ovulation, parturition and lactation in female mammals. More particularly, the present invention is directed to a method of administering a dopamine $D_2$ receptor antagonist, such as domperidone, to a female mammal for altering hormonal levels in the animal in order to promote ovulation, parturition or lactation.

BACKGROUND OF THE INVENTION

Breeders of various animals, such as horses and other livestock, face many problems in getting the animals to breed properly. For instance, some female mammals fail to ovulate and fall into heat in regular intervals. Mammals that exhibit a prolonged period of inactivity between two periods of heat are described as being anestrous. Anestrous female mammals will not accept the male and are incapable of conceiving offspring.

Another problem breeders experience is the inability of some mammals to prepare for and give birth after the mammals have become pregnant and the fetus is ready to be born. In preparation for and during the act of giving birth, a process known as parturition, the pregnant mammal should experience cervical relaxation, swelling of the vulva, and relaxation of ligaments around the pelvis. Without these events occurring, the mammal is not capable of giving natural, unassisted birth. Further, should these events not occur, the health of the mother and of the unborn offspring are at grave risk.

Another problem commonly experienced by breeders is the inability of mammals to produce and secrete milk after giving birth. The condition of failing to lactate properly after child birth is referred to as agalactia, and is especially prevalent in mares and other livestock. Should the mammal not lactate properly, the offspring must then be bottle fed which is time consuming, labor intensive, and significantly adds to the cost of raising the livestock.

Each of the problems mentioned above can be caused to a great extent by hormonal imbalance or by hormonal irregularities. Hormones released in the body are primarily responsible for initiating ovulation, parturition, and lactation in mammals. Thus, if hormones are not released in the body at particular critical times, the above described problems can be experienced.

For instance, hormones can be prevented from being released in the body by various chemical agents. One such known chemical agent is dopamine. Dopamine is a decarboxylated form of dopa. Dopamine is believed to be produced by the body when it is necessary to suppress hormone secretion. Dopamine suppresses hormone release by binding to and tying up receptors on the anterior pituitary, an endocrine gland located at the base of the brain not far from the hypothalamus. By binding to the anterior pituitary, the gland is prevented from receiving a stimulus hormone that causes it to release other hormones such as those necessary for ovulation, parturition, and lactation.

Although dopamine is necessary during particular periods for keeping hormone levels in the body within controlled ranges, excess levels of dopamine can adversely interfere with the process of reproduction. Also, besides dopamine, there are other chemical agents that can interfere with or prevent hormone secretion, adversely affecting biological processes.

Thus, a need exists for a method of promoting follicular growth and ovulation, parturition, and lactation in female mammals. A need also exists for treating anestrous mammals, agalactic mammals, and mammals that fail to prepare for parturition when a fetus is ready to be born. A further need exists for a chemical agent that antagonizes dopamine and other chemicals that act in a similar manner in order to counteract hormonal imbalance and irregularities.

SUMMARY OF THE INVENTION

The present invention recognizes and addresses the foregoing disadvantages, and others of prior art constructions and methods.

Accordingly, it is an object of the present invention to provide a process for promoting ovulation and for treating anestrous mammals.

Another object of the present invention is to provide a method for promoting parturition in a pregnant mammal that is at the end of the pregnancy cycle.

It is another object of the present invention to provide a process for promoting lactation and for treating agalactia in mammals that have just given birth.

Still another object of the present invention is to provide a process for controlling hormonal release in the body.

Another object of the present invention is to provide a method for altering hormone levels in the body of a mammal by administering to the mammal a dopamine antagonist.

It is another object of the present invention to provide a process for treating a mammal that has excess levels of dopamine and other similar acting agents within its body.

These and other objects of the present invention are achieved by providing a method for promoting follicular growth and ovulation, for preparing a mammal for parturition, and for promoting lactation by administering to a female mammal a composition. The composition contains a dopamine $D_2$ receptor antagonist. For instance, in one embodiment, the composition can contain domperidone.

The present inventor has used domperidone in the past for treating animals suffering from fescue toxicosis. For instance, the present inventor's prior work is disclosed in U.S. Pat. No. 5,372,818 entitled "Method of Treating Fescue Toxicosis with Domperidone", which is incorporated herein by reference in its entirety. In U.S. Pat. No. 5,372,818, it was discovered not only that domperidone is an effective agent for treating fescue toxicosis, but that domperidone does not substantially cross the blood brain barrier. Therefore, domperidone can be administered to animals while avoiding substantial adverse behavioral and neurological side effects. Such neuroleptic side effects have been observed in animals exposed to other $D_2$ receptor antagonists such as the drugs, metoclopramide and sulpiride.

Although U.S. Pat. No. 5,372,818 provides great advances in the art for treating animals infected with fescue toxicosis, various advantages, aspects and features of the present invention remain absent from the present inventor's prior patent.

According to the present invention, ovulation, parturition or lactation can be promoted by administering to a mammal a composition containing a dopamine $D_2$ receptor antagonist, such as domperidone. The $D_2$ receptor antagonist can be administered to the mammal in an amount from about 0.08 mg to about 3.3 mg per kilogram of body weight of the mammal. The $D_2$ receptor antagonist can be administered to the mammal either orally or subcutaneously.

Specifically, when using domperidone to promote follicular growth and ovulation, domperidone can be orally administered at a concentration of from about 0.2 mg to about 3.3 mg per kilogram weight of said mammal. In one preferred embodiment, the dosage of domperidone is about 0.55 mg per kilogram weight of the mammal.

When administered subcutaneously, the dosage can be from about 0.08 mg to about 1.32 mg and particularly around 0.22 mg per kilogram weight of the mammal.

When attempting to promote parturition, udder development, and lactation, on the other hand, domperidone can be administered orally to a mammal at a dosage of from about 0.2 mg to about 3.3 mg and particularly at about 1.1 mg per kilogram weight of the mammal. When administered subcutaneously, the dosage of domperidone can be from about 0.08 mg to about 1.32 mg and particularly at about 0.44 mg per kilogram weight of the mammal.

All of the above dosage levels according to the present invention can be given daily. Although unknown, it is believed that the treatments cause hormonal levels in the mammal to change for promoting either ovulation, parturition or lactation. Unexpectedly, it has also been discovered that a dopamine $D_2$ receptor antagonist such as domperidone may also cause an increase in feed intake in the mammal resulting in weight increases.

Other objects, features and aspects of the present invention are discussed in greater detail below.

DETAILED DESCRIPTION OF PREFERRED EMBODIMENTS

It is to be understood by one of ordinary skill in the art that the present discussion is a description of exemplary embodiments only, and is not intended as limiting the broader aspects of the present invention, which broader aspects are embodied in the exemplary construction.

The present invention is generally directed to various processes and methods for promoting and stimulating follicular growth and ovulation, for preparing a mammal for parturition, and for promoting and stimulating udder development and lactation. The process of the present invention can be used to treat anestrous mammals, agalactic mammals, and more generally any mammal experiencing problems during the reproductive cycle. The process of the present invention can also be used to manipulate and control ovulation and lactation. For instance, in mammals that only ovulate seasonally, the present invention can be used to promote ovulation at times when ovulation would not normally occur.

In general, the objects and advantages of the present invention are achieved by administering to a female mammal a composition containing a dopamine $D_2$ receptor antagonist. A $D_2$ receptor antagonist should be chosen but does not substantially cross the blood brain barrier in order to ensure that the mammal does not suffer any adverse behavioral or neurological side effects. For instance, in a preferred embodiment, the dopamine $D_2$ receptor antagonist is domperidone.

Although unknown, it is believed that domperidone ties up receptor cells in the anterior pituitary and other places in the body preventing various chemical agents, such as dopamine, from binding to the receptor cells and altering the release of hormones throughout the body. By altering the effects of dopamine and other similar agents, domperidone allows the anterior pituitary and other glands of the body to secrete hormones necessary for ovulation, parturition, and lactation as will be described in greater detail hereinafter.

As discussed above, one embodiment of the present invention is directed to a process for stimulating and promoting follicular growth and ovulation. The process can be used to treat anestrous mammals, to cause a mammal to ovulate out of season, or to otherwise control when ovulation occurs.

The process of the present invention can be used to treat any mammal, but is particularly applicable to livestock. For instance, many problems have been experienced in attempting to get horses to breed. Further, mares only ovulate and fall into heat during particular times of the year. The process of the present invention cannot only be used to treat horses that experience problems ovulating but can also be used to breed horses during times of the year when it was not before possible.

According to the present invention, follicular growth and ovulation is promoted by administering to a mammal a dopamine $D_2$ receptor antagonist. In one preferred embodiment, the dopamine $D_2$ receptor antagonist is domperidone. The $D_2$ receptor antagonist can be taken orally by the mammal or can be injected subcutaneously.

In one embodiment, when using domperidone, it has been found that ovulation is promoted when the domperidone is taken orally by a mammal in an amount from about 0.2 mg/kg (mg of domperidone per kg of body weight) to about 3.3 mg/kg. At concentrations greater than 3.3 mg/kg, no further benefits have been observed. Thus far, the best results have been obtained when domperidone has been taken orally at a concentration of about 0.55 mg/kg.

If the domperidone is injected subcutaneously into the mammal, the dosages listed above can be reduced to about 40% of the oral dose. Thus, if injected into a mammal, domperidone can be administered at a concentration of from about 0.08 mg/kg to about 1.32 mg/kg, with a preferred concentration of about 0.22 mg/kg.

Ovulation is the process by which an egg is discharged from a follicle of an ovary and is released into the fallopian tube and the uterus. More particularly, in mammals, as eggs mature in the ovary, the eggs are surrounded by a layer of follicular cells creating a fluid filled follicle. As the egg reaches maturity, the fluid filled follicle bulges from the surface of the ovary. Stimulated by a hormone, ovulation occurs when the follicle ruptures, releasing the egg.

Ovarian cycles are initiated and controlled by a variety of hormones secreted throughout the body. Specifically, these hormones include follicle stimulating hormone (FSH) which is secreted by the pituitary gland and which stimulates follicular and egg growth. Luteinizing hormone (LH), which is also released from the pituitary gland, stimulates the follicle to secrete estrogen which causes the walls of the uterine to thicken. LH also triggers ovulation causing the follicle to rupture.

The levels and frequency of release of these hormones can be altered in the body by various chemical agents such as dopamine. Although unknown, it is believed that the $D_2$ receptor antagonists of the present invention, such as domperidone, neutralize the effects of dopamine and other related chemical agents. By administering to a mammal a $D_2$ receptor antagonist, LH and FSH can be released by the body without inhibition causing ovulation to occur.

Besides promoting ovulation, the present invention is also directed to a process for preparing a mammal for parturition. This process is for treating mammals and particularly livestock that have problems giving birth once pregnant.

Parturition is stimulated in a mammal according to the present invention by administering to the mammal a composition containing a dopamine $D_2$ receptor antagonist. For instance, in one embodiment, the composition can contain domperidone. Once administered to the mammal, it is believed that the composition neutralizes the effects of dopamine and other similar chemical agents from altering the release of hormones that prepare a mammal for giving birth. Thus, the composition of the present invention allows the body to secrete hormones that may affect cervical dilation and general broodiness.

By administering the composition to pregnant mammals, the mammal is more likely to give birth on time. The composition also promotes natural births and prevents against having to deliver the offspring by C-sections. The treatment not only protects the unborn offspring during delivery but also protects the pregnant mother from being harmed during birth.

In order to promote normal parturition, in one embodiment, a pregnant mammal can be orally fed domperidone at a concentration of from about 0.2 mg/kg of body weight to about 3.3 mg/kg. In one preferred embodiment, the oral dosage can be about 1.1 mg/kg.

When injected subcutaneously into the mammal, domperidone has been found to produce effective results at concentrations of from about 0.08 mg/kg to about 1.32 mg/kg, with best results being obtained at about 0.44 mg/kg. Amounts greater than 1.32 mg/kg can be administered to the animal without any adverse side effects. Additional benefits, however, have not been observed at higher dosage levels.

Whether administered orally or subcutaneously, treatments of the $D_2$ receptor antagonist administered to the mammal can begin at any time during the pregnancy. For larger livestock such as cattle and horses, the treatment should begin about fifteen to twenty days prior to the expected birth date.

A further embodiment of the present invention is directed to a process for promoting udder development and lactation in female mammals. The process can be used to prevent or treat agalactia or any other ailments regarding the low level or non-production of milk. For instance, lactation problems have been particularly observed in mares that have recently given birth. After giving birth, many mares either fail to produce milk or do not produce enough milk to adequately nurture the foal. When this occurs, the foal must be bottle fed or fed in some other manner which significantly adds to the expense of raising the livestock.

The process of the present invention can be used in these circumstances to stimulate or increase milk production in non-milking mares and other mammals. Further, the process can be used simply to increase milk production without any adverse effects. For instance, the process of the present invention can also be used to increase the quantity of milk obtained from cows for human consumption.

Lactation is stimulated and promoted according to the present invention by administering to mammals a composition containing a dopamine $D_2$ receptor antagonist. For instance, the composition can contain domperidone in an amount sufficient to stimulate milk production.

In one embodiment, milk production was stimulated in horses by orally administering to the horses domperidone in a concentration of from about 0.2 mg/kg of body weight to about 3.3 mg/kg of body weight, and particularly at a concentration of about 1.1 mg/kg. At oral dosages greater than 3.3 mg/kg, no further beneficial results were observed.

Domperidone can also be administered to the animal subcutaneously. If injected into the mammal, about 40% of the dosage amounts given above can be used. Thus, when injected subcutaneously, the domperidone concentration can be from about 0.08 mg/kg to about 1.32 mg/kg.

Although unknown, it is believed that the dopamine $D_2$ receptor antagonist, such as domperidone, influences hormonal levels within the animal. Domperidone is believed to alter hormone levels by neutralizing the effect of dopamine-like agents that prevent particular hormones from being secreted. With respect to lactation, it is believed that the dopamine $D_2$ receptor antagonist increases the levels of progesterone, estrogen and prolactin within the body of the mammal. These hormones are believed to be primarily responsible for promoting udder development and lactation.

Besides promoting ovulation, preparing a mammal for parturition, and stimulating lactation, it has also been unexpectedly discovered that the composition of the present invention can cause a mammal to increase its feed intake and thus gain weight faster. This process is particularly beneficial in raising livestock for human consumption.

In order to increase feed intake according to the present invention, a dopamine $D_2$ receptor antagonist, such as domperidone, is administered to a mammal. The treatment can be given to the mammal orally or subcutaneously. If domperidone is used and administered orally, the domperidone should be fed to the mammal at a concentration of from about 0.2 mg/kg of body weight to about 3.3 mg/kg of body weight and particularly at about 1.1 mg/kg. If domperidone is injected into the mammal, the dosage should be from about 0.08 mg/kg to about 1.32 mg/kg.

At the present time, it is unknown why domperidone causes increases in feed intake. It is believed, however, that domperidone may stimulate feed intake by increasing levels of the hormone prolactin in the body of the mammal. It may also be possible that domperidone causes levels of hormones to be altered that firm up the gut of the mammal. If the muscles of the gut were to be stimulated, then food passage may increase in the gut allowing the animal to eat more.

In general, in delivering an effective dosage of a dopamine $D_2$ receptor antagonist to a mammal according to the present invention, various vehicles may be used. For instance, when taken orally, the $D_2$ receptor antagonist may be combined with a feed or feed supplement material as the carrier. If injected, the drug may be mixed with any suitable carrier. Additionally, the $D_2$ receptor antagonist, such as domperidone, may be added to salt blocks or mineral blocks during casting or mixed directly into feed. Further, various other administration techniques well known in the art may be employed. It is to be understood that the present invention is not to be limited to any particular vehicle.

It also should be appreciated that although the above description and following examples relate primarily to livestock such as horses and cattle, it is believed that the drug will work as described with any mammal. For instance, although untested at the present time, it is believed that a dopamine $D_2$ receptor antagonist that does not substantially cross the blood brain barrier such as domperidone may be administered to humans for promoting ovulation, facilitating childbirth, or stimulating lactation.

The present invention may be better understood with reference to the following examples.

EXAMPLE NO. 1

The following tests were performed in order to demonstrate the ability of domperidone to stimulate and promote ovulation in mares.

Ten mares were fed a composition containing domperidone at a concentration of 0.55 mg/kg of body weight. The composition was administered daily. Specifically, the domperidone was mixed with molasses and fed to the mares with a 5 cc syringe. Nine additional mares were used as a control. These mares were fed the molasses carrier not containing any domperidone.

Of importance, the treatments were carried out in January and February during a time when mares typically do not ovulate. The following results were obtained:

TABLE 1

Effect of Domperidone on Follicular Growth and Ovulation

| Test No. | Treated with Domperidone at .55 mg/kg | No. of Days of Treatment | Date of Ovulation | No. of Days of Treatment Before Ovulation |
|---|---|---|---|---|
| 1 | No | 45 | d/n ovulate | d/n ovulate |
| 2 | No | 45 | d/n ovulate | d/n ovulate |
| 3 | No | 45 | d/n ovulate | d/n ovulate |
| 4 | No | 25 | Feb. 26 | 25 |
| 5 | No | 45 | d/n ovulate | d/n ovulate |
| 6 | No | 45 | d/n ovulate | d/n ovulate |
| 7 | No | 45 | d/n ovulate | d/n ovulate |
| 8 | No | 37 | Mar. 10 | 37 |
| 9 | No | 45 | d/n ovulate | d/n ovulate |
| 10 | Yes | 18 | Feb. 9 | 18 |
| 11 | Yes | 15 | Feb. 6 | 18 |
| 12 | Yes | 21 | Feb. 12 | 21 |
| 13 | Yes | 17 | Feb. 8 | 17 |
| 14 | Yes | 24 | Feb. 15 | 24 |
| 15 | Yes | 14 | Feb. 5 | 14 |
| 16 | Yes | 16 | Feb. 7 | 16 |
| 17 | Yes | 22 | Feb. 13 | 22 |
| 18 | Yes | 45 | d/n ovulate | d/n ovulate |
| 19 | Yes | 19 | Feb. 10 | 19 |

As shown above, only two of the control mares ovulated. In comparison, nine of the ten mares treated with domperidone ovulated. Also of significance, the treated mares ovulated during the early part of February. No neurological side effects were observed in any of the mares treated with domperidone during the study.

EXAMPLE NO. 2

The following tests were performed to demonstrate the ability of domperidone to prepare a mammal for parturition and to stimulate udder development and lactation.

Twelve known agalactic mares who were either pregnant or had just given birth were treated with domperidone. The domperidone was administered orally at a dosage of 1.1 mg/kg of body weight per day. All of the mares treated were not suffering from fescue toxicosis. The following results were obtained:

TABLE 2

Effect of Domperidone on Preparation for Parturition, Udder Development and Lactation In Mares

| Test No. | Days Before (−) or After Expected Foaling Dosing Was Initiated | Days Before (−) or After Expected Foaling that Mare Foaled | Mare's Udder Development Before Treatment Began | Mare's Udder Development After Treatment Began | Was Mare Lactating Normally After Foaling? | Did Mare Have A Live Foal? |
|---|---|---|---|---|---|---|
| 1 | +5 | +12 | Very Little | Dripping Milk 5th Day of Treatment | Yes | Yes |
| 2 | −28 | −1 | Very Little | Increased Weekly | Yes | Yes |

TABLE 2-continued

Effect of Domperidone on Preparation for Parturition, Udder Development and Lactation In Mares

| Test No. | Days Before (−) or After Expected Foaling Dosing Was Initiated | Days Before (−) or After Expected Foaling that Mare Foaled | Mare's Udder Development Before Treatment Began | Mare's Udder Development After Treatment Began | Was Mare Lactating Normally After Foaling? | Did Mare Have A Live Foal? |
|---|---|---|---|---|---|---|
| 3 | No data | +8 | No Development | After 2 Days, Made Udder Sack | Yes | Yes |
| 4 | +6 | +15 | Very Little | Developed Slowly But Natural | Yes | Yes |
| 5 | +4 | +14 | Virtually No Udder | Developed Adequately | No. but drug helped some | Yes |
| 6 | −21 | 0 | Normal | Normal | Yes | Yes |
| 7 | +5 | No data | Incomplete Small Udder | Udder Developed As Soon As Treatment Started | Yes | Yes |
| 8 | −24 | −3 | No Development | Very Slight Development | Yes | Yes |
| 9 | No data | +3 | Minimal | Gradual Development | Yes | Yes |
| 10 | −13 | No data | Slight Base; No Filling of Teat | Normal Development | Yes | Yes |
| 11 | −20 | −3 | No Development | No Response | Yes | Yes |
| 12 | −10 | −2 | None to Minimal | Immediate Development After Treatment | Yes | Yes |

EXAMPLE NO. 3

It has also been unexpectedly discovered that treating a mammal with a $D_2$ receptor antagonist, such as domperidone, increases feed intake. The following results demonstrate this phenomenon.

Ten quarter horse mares were housed in individual pens and fed a standard feed concentrate weighing 0.5% of each mares' initial body weight at approximately 8:00 A.M. each day during the study. In addition, hay was fed to the mare ad libitum each day. During the night, the mares were placed in a dry lot having no access to food.

After seven days on the above feed schedule (control), the mares were orally fed at 8:00 A.M. each day domperidone at a dosage of 1.1 mg/kg of body weight. The domperidone was fed to the mares in a molasses carrier. During treatment with domperidone, the mares were fed the concentrate feed and hay in the same manner as during the control period. Domperidone was fed to the mares for two weeks. The following results were obtained:

TABLE 3

Effect of Domperidone On The Daily Feed Intake of Mares

| Mare ID | Initial Body Weight (lbs) | Concentrate Feed (lbs) | Avg. Hay Consumption Before Treatment (lbs) | Avg. Hay Consumption After Treatment (lbs) |
|---|---|---|---|---|
| 1 | 1025 | 5.1 | 11.2 | 13.0 |
| 2 | 980 | 4.9 | 10.3 | 12.2 |
| 3 | 1110 | 5.6 | 12.2 | 14.1 |
| 4 | 900 | 4.5 | 11.1 | 13.2 |
| 5 | 1050 | 5.3 | 12.0 | 14.1 |
| 6 | 1000 | 5.0 | 11.0 | 14.2 |
| 7 | 980 | 4.9 | 9.8 | 12.3 |
| 8 | 1010 | 5.1 | 11.0 | 13.5 |
| 9 | 1100 | 5.5 | 12.5 | 15.0 |
| 10 | 950 | 4.8 | 10.2 | 12.1 |

As shown above, daily hay consumption increased for each of the ten mares after treatment with domperidone began.

These and other modifications and variations to the present invention may be practiced by those of ordinary skill in the art, without departing from the spirit and scope of the present invention, which is more particularly set forth in the appended claims. In addition, it should be understood that aspects of the various embodiments may be interchanged both in whole or in part. Furthermore, those of ordinary skill in the art will appreciate that the foregoing description is by way of example only, and is not intended to limit the invention so further described in such appended claims.

What is claimed:

1. A method for promoting parturition in animals comprising the step of:

administering to a pregnant female animal not suffering from fescue toxicosis a composition comprising domperidone, said domperidone being administered to said pregnant animal in an amount sufficient to promote parturition.

2. A method as defined in claim 1, wherein said domperidone is administered to said pregnant animal in an amount from about 0.08 mg to about 3.3 mg per kilogram weight of said weight.

3. A method as defined in claim 1, wherein said composition is administered orally.

4. A method as defined in claim 1, wherein said composition is administered subcutaneously.

5. A method as defined in claim 3, wherein said composition is administered orally to said pregnant animal in an amount from about 0.2 mg to about 3.3 mg per kilogram weight of said animal.

6. A method as defined in claim 4, wherein said composition is administered subcutaneously to said pregnant animal in an amount from about 0.08 mg to about 1.32 mg per kilogram weight of said animal.

7. A method as defined in claim 1, wherein said pregnant animal is an animal selected from the group consisting of a mare or a cow.

* * * * *